United States Patent [19]

Ito et al.

[11] Patent Number: 5,049,748
[45] Date of Patent: Sep. 17, 1991

[54] METHOD AND APPARATUS FOR FORMING ENERGY SUBTRACTION IMAGES

[75] Inventors: Wataru Ito; Makoto Ohgoda; Yasuhiko Goto; Kazuo Horikawa, all of Kanagawa, Japan

[73] Assignee: Fuji Photo Film Co. Ltd., Kanagawa, Japan

[21] Appl. No.: 599,925

[22] Filed: Oct. 19, 1990

[30] Foreign Application Priority Data

Oct. 19, 1989 [JP] Japan .................................. 1-272214
Oct. 19, 1989 [JP] Japan .................................. 1-272217
Oct. 19, 1989 [JP] Japan .................................. 1-272218

[51] Int. Cl.$^5$ ........................................... G03B 42/02
[52] U.S. Cl. .................................. 250/327.2; 378/62; 378/99
[58] Field of Search .................. 364/413.23; 358/111; 378/99, 62; 250/327.2 C, 484.1 B

[56] References Cited

U.S. PATENT DOCUMENTS

| | | | |
|---|---|---|---|
| 4,258,264 | 3/1981 | Kotera et al. | 250/484.1 |
| 4,335,427 | 6/1982 | Hunt et al. | 364/413.23 |
| 4,559,557 | 12/1985 | Keyes et al. | 358/111 |
| 4,590,517 | 5/1986 | Kato et al. | 358/111 |
| 4,644,582 | 2/1987 | Morishita et al. | 382/6 |
| 4,851,984 | 7/1989 | Doi et al. | 364/413.23 |
| 4,855,598 | 8/1989 | Ohgoda et al. | 250/327.2 |

FOREIGN PATENT DOCUMENTS

58-163339  9/1983  Japan .
2153180  8/1985  United Kingdom ............... 358/111

Primary Examiner—Constantine Hannaher
Attorney, Agent, or Firm—Sughrue, Mion, Zinn, Macpeak & Seas

[57] ABSTRACT

Digital image signals are detected from radiation images of an object constituted of bones and soft tissues. A subtraction process is carried out with a predetermined parameter on the digital image signals, and a difference signal representing an image of part of the object is obtained. Each of images of a phantom, which has part exhibiting an equivalent radiation absorption coefficient to bones and/or part exhibiting an equivalent radiation absorption coefficient to soft tissues, is read out together with each object image. A value of the parameter is found, with which the image of either part of the phantom becomes erased in a subtraction image of the phantom obtained from subtraction processing. The value of the parameter, which has thus been found, is determined as an optimum value of the parameter. Subtraction processing is then carried out by using the optimum value of the parameter.

34 Claims, 4 Drawing Sheets

METHOD AND APPARATUS FOR FORMING ENERGY SUBTRACTION IMAGES

BACKGROUND OF THE INVENTION

1. Field of the Invention

This invention relates to a method for forming an energy subtraction image wherein a parameter is optimized which is used when subtraction processing, in particular, digital subtraction processing, is carried out on radiation images, and an apparatus for carrying out the method.

2. Description of the Prior Art

Techniques for carrying out digital subtraction processing on radiation images have heretofore been known. When digital subtraction processing is to be carried out, two radiation images recorded under different conditions are photoelectrically read out, and digital image signals which represent the radiation images are obtained. The image signal components of the digital image signals which represent corresponding picture elements in the radiation images are then subtracted from each other with a predetermined parameter, and a difference signal is thereby obtained which represents the image of a specific structure or part of the object represented by the radiation images. With the subtraction processing method, two digital image signals are subtracted from each other in order to obtain a difference signal, and the radiation image of a specific structure can be reproduced from the difference signal.

Basically, subtraction processing is carried out with either the so-called temporal (time difference) subtraction processing method or the so-called energy subtraction processing method. In the former method, in order to extract the image of a specific structure of an object from the image of the whole object, the image signal representing a radiation image obtained without injection of contrast media is subtracted from the image signal representing a radiation image in which the image of the specific structure of the object is enhanced by the injection of contrast media. In the latter method, such characteristics are utilized that a specific structure of an object exhibits specific radiation energy absorbing characteristics. Specifically, an object is exposed to several kinds of radiation with different energy distributions. In this manner, two radiation images, in which different images of a specific structure are embedded, are obtained. Thereafter, the image signals representing the two radiation images are weighted appropriately, i.e. an appropriate value of the parameter for a subtraction process is determined, and the weighted image signals are subjected to a subtraction process. The image of the specific structure is thereby extracted.

Subtraction processing is extremely effective, particularly for medical diagnosis utilizing image processing of X-ray images, and electronics research has continued to develop improved subtraction processing methods.

By carrying out energy subtraction processing on radiation images of an object constituted of bones and soft tissues, a subtraction image can be obtained in which the patterns of the bones have been erased and only the patterns of the soft tissues have been extracted. (Such a subtraction image will hereinbelow be referred to as the "soft tissue image".) Alternatively, a subtraction image can be obtained in which the patterns of the soft tissues have been erased and only the patterns of the bones have been extracted. (Such a subtraction image will hereinbelow be referred to as the "bone image".)

However, in such cases, the value of the parameter is not necessarily suitable for every subtraction process or for the whole area of the image. This is presumably because the level of radiation energy fluctuates due to, for example, fluctuations in the X-ray tube voltage for different exposures to the radiation, and the effective radiation absorption coefficient varies for parts of the object having different thicknesses due to non-monochromaticity of the X-rays.

SUMMARY OF THE INVENTION

The primary object of the present invention is to provide a method for forming an energy subtraction image wherein a parameter used during subtraction processing is optimized such that a soft tissue image or a bone image having good image quality may be obtained from every subtraction processes, and/or a soft tissue image or a bone image having good image quality over the whole area of the image may be obtained.

Another object of the present invention is to provide an apparatus for carrying out the method for forming an energy subtraction image.

The present invention provides a first method for forming an energy subtraction image during energy subtraction processing wherein a plurality of radiation images of an object constituted of bones and soft tissues, which radiation images have been formed with at least two kinds of radiation having different energy distributions and having passed through the object and in which different images of at least part of the object are embedded, are read out and converted into a plurality of digital image signals, each of which is made up of a series of image signal components, the image signal components of the digital image signals which represent corresponding picture elements in the plurality of the radiation images are then subtracted from each other with a predetermined parameter, and a difference signal representing an image, in which the patterns of the bones or the patterns of the soft tissues represented by the radiation images have been erased, is thereby obtained, the method for forming an energy subtraction image comprising the steps of:

i) during the operation for reading out each of said radiation images, simultaneously reading out each of a plurality of images of a phantom, which at least has part exhibiting an equivalent radiation absorption coefficient to said bones and/or part exhibiting an equivalent radiation absorption coefficient to said soft tissues, together with the image of the object, ii) finding a value of the parameter, with which the image of the part of said phantom exhibiting an equivalent radiation absorption coefficient to said bones or the image of the part of said phantom exhibiting an equivalent radiation absorption coefficient to said soft tissues, whichever image is to be erased, becomes erased in a subtraction image of said phantom obtained from subtraction processing, iii) determining the value of the parameter, which has thus been found, as an optimum value of the parameter, and iv) carrying out subtraction processing by using said optimum value of the parameter.

The present invention also provides a first apparatus for forming an energy subtraction image, which comprises:

i) an image read-out means for reading out each of a plurality of radiation images of a phantom, which at least has part exhibiting an equivalent radiation absorption coefficient to said bones and/or part exhibiting an equivalent radiation absorption coefficient to said soft tissues, together with each of a plurality of radiation images of an object, and converting these radiation images into digital image signals, ii) an optimum parameter value determining means for finding a value of a parameter for a subtraction process, with which value the image of the part of said phantom exhibiting an equivalent radiation absorption coefficient to said bones or the image of the part of said phantom exhibiting an equivalent radiation absorption coefficient to said soft tissues, whichever image is to be erased, becomes erased in a subtraction image, which is obtained from subtraction processing carried out on regions in which said radiation images of said phantom were recorded, and determining the value of the parameter, which has thus been found, as an optimum value of the parameter, and iii) a subtracting operation means for:
  after the plurality of said radiation images of said object constituted of bones and soft tissues, which radiation images have been formed with at least two kinds of radiation having different energy distributions and having passed through said object and in which different images of at least part of said object are embedded, are read out by said image read-out means and converted thereby into a plurality of digital image signals, each of which is made up of a series of image signal components,
  subtracting the image signal components of the digital image signals from each other by using said optimum value of the parameter, which image signal components represent corresponding picture elements in the plurality of said radiation images, and thereby generating a difference signal representing an image, in which the patterns of the bones or the patterns of the soft tissues represented by said radiation images have been erased.

In the first method and apparatus for forming an energy subtraction image in accordance with the present invention, radiation images may be read out with one of various methods. By way of example, radiation images may be stored on stimulable phosphor sheets. The radiation images, which have been stored on the stimulable phosphor sheets may then be read out from an image read-out operation wherein each stimulable phosphor sheet is scanned with stimulating rays, which cause it to emit light in proportion to the amount of energy stored thereon during its exposure to radiation, and the emitted light is detected photoelectrically. Alternatively, an image intensifier may be used during the operation for reading out a radiation image. As another alternative, a film digitizer may be used during the operation for reading out a radiation image.

One of the methods utilizing stimulable phosphor sheets is proposed in, for example, U.S. Pat. No. 4,590,517. In the proposed method, stimulable phosphor sheets are used, on which radiation images can be recorded even when the energy intensity of the radiation to which the stimulable phosphor sheets are exposed varies over a wide range. The stimulable phosphor sheets are exposed to radiation, which has passed through an object, under different conditions, and a plurality of radiation images, in which different images of a specific structure of the object are embedded, are thereby stored on the stimulable phosphor sheets. Each of the stimulable phosphor sheet is then exposed to stimulating rays, which cause is to emit light in portion to the amount of energy stored thereon during its exposure to the radiation, and the emitted light is detected and converted into a digital image signal.

As disclosed in, for example, U.S. Pat. No. 4,258,264, when certain kinds of phosphors are exposed to radiation such as X-rays, $\alpha$-rays, $\beta$-rays, $\gamma$-rays, cathode rays or ultraviolet rays, they store part of the energy of the radiation. Then, when the phosphor which has been exposed to the radiation is exposed to stimulating rays such as visible light, light is emitted by the phosphor in proportion to the amount of energy stored thereon during its exposure to the radiation. A phosphor exhibiting such properties is referred to as a stimulable phosphor. A sheet provided with a layer of the stimulable phosphor is referred to as the stimulable phosphor sheet.

On stimulable phosphor sheets, images can be recorded even when the energy intensity of the radiation to which the stimulable phosphor sheets are exposed varies over a wide range. Also, the stimulable phosphor sheets provide very good resolution. Therefore, in cases where digital subtraction processing is carried out on radiation images stored on stimulable phosphor sheets, even if the radiation doses to the stimulable phosphor sheets fluctuate during the operations for recording the radiation images, a subtraction image can be obtained which has good image quality and can serve as an effective tool in, particularly, the efficient and accurate diagnosis of an illness.

The phantom used in the first method and apparatus for forming an energy subtraction image at least has part exhibiting an equivalent radiation absorption coefficient to bones and/or part exhibiting an equivalent radiation absorption coefficient to soft tissues. No limitation is imposed on the shape of the phantom. The phantom should preferably have a thin filter-like shape. In such cases, the phantom can be easily adhered to a stimulable phosphor sheet, a cassette in which stimulable phosphor sheets are housed, or an object supporting member on which an object is placed.

Also, the phantom may be constituted such that the part exhibiting an equivalent radiation absorption coefficient to bones is located in the middle area of the phantom, and the part exhibiting an equivalent radiation absorption coefficient to soft tissues is located in the surrounding areas. Such a phantom is suitable for the formation of a subtraction image in which the bone patterns have been erased. Alternatively, the phantom may be constituted such that the part exhibiting an equivalent radiation absorption coefficient to soft tissues is located in the middle area of the phantom, and the part exhibiting an equivalent radiation absorption coefficient to bones is located in the surrounding areas. Such a phantom is suitable for the formation of a subtraction image in which the soft tissue patterns have been erased.

As another alternative, the phantom may be provided with a plurality of parts exhibiting radiation absorption coefficients which change step-wise and which are equivalent to those of various substances, including the bones and soft tissues. When such a phantom is used, a value of the parameter can be determined, with which an image of a certain part of the phantom equivalent to an arbitrary substance whose image is to be erased can be erased in a subtraction image. Therefore, a subtraction image can be formed in which the image of an arbitrary substance has been erased.

With the first method for forming an energy subtraction image in accordance with the present invention, the optimum value of the parameter is determined by using the phantom. Thereafter, subtraction processing is carried out with the optimum value of the parameter. Therefore, a subtraction image can be formed which is suitable for diagnosis. Also, even if the level of radiation energy fluctuates during the image recording operations, due to, for example, fluctuations in the X-ray tube voltage for different exposures to the radiation, a subtraction image having good image quality can be obtained.

The present invention further provides a second method for forming an energy subtraction image during energy subtraction processing wherein a plurality of radiation images of an object constituted of bones and soft tissues, which radiation images have been formed with at least two kinds of radiation having different energy distributions and having passed through the object and in which different images of at least part of the object are embedded, are read out and converted into a plurality of digital image signals, each of which is made up of a series of image signal components, the image signal components of the digital image signals which represent corresponding picture elements in the plurality of the radiation images are then subtracted from each other with a predetermined parameter, and a difference signal representing an image, in which the patterns of the bones or the patterns of the soft tissues represented by the radiation images have been erased, is thereby obtained, the method for forming an energy subtraction image comprising the steps of:
i) dividing each of said radiation images into a plurality of blocks,
ii) determining an optimum temporary value of the parameter for each of said blocks,
iii) determining a final value of the parameter for each of picture elements of the radiation image by carrying out a smoothing process on the temporary values of the parameter, which have been determined for the plurality of said blocks, such that the value of the parameter changes continuously between adjacent picture elements, and
iv) carrying out subtraction processing by using the final values of the parameter which have been determined for the picture elements.

The present invention still further provides a second apparatus for forming an energy subtraction image, which comprises:
i) an image read-out means for reading out radiation images and converting them into digital image signals,
ii) a temporary parameter value determining means for determining an optimum temporary value of a parameter for a subtraction process, said temporary value of the parameter being determined for each of blocks, into which each of said radiation images has been divided,
iii) a final parameter value determining means for determining a final value of the parameter for each of picture elements of the radiation image by carrying out a smoothing process on the temporary values of the parameter, which have been determined for the plurality of said blocks, such that the value of the parameter changes continuously between adjacent picture elements, and
iv) a subtracting operation means for:
after a plurality of radiation images of an object constituted of bones and soft tissues, which radiation images have been formed with at least two kinds of radiation having different energy distributions and having passed through said object and in which different images of at least part of said object are embedded, are read out by said image read-out means and converted thereby into a plurality of digital image signals, each of which is made up of a series of image signal components,
subtracting the image signal components of the digital image signals from each other by using said final values of the parameter, which image signal components represent corresponding picture elements in the plurality of said radiation images, and thereby generating a difference signal representing an image, in which the patterns of the bones or the patterns of the soft tissues represented by said radiation images have been erased.

In the second method and apparatus for forming an energy subtraction image in accordance with the present invention, radiation images may be read out with one of various methods. By way of example, radiation images may be stored on stimulable phosphor sheets. The radiation images, which have been stored on the stimulable phosphor sheets may then be red out from an image read-out operation wherein each stimulable phosphor sheet is scanned with stimulating rays, which cause it to emit light in proportion to the amount of energy stored thereon during its exposure to radiation, and the emitted light is detected photoelectrically. Alternatively, an image intensifier may be used during the operation for reading out a radiation image. As another alternative, a film digitizer may be used during the operation for reading out a radiation image.

In the second method for forming an energy subtraction image in accordance with the present invention, the optimum temporary value of the parameter for each of the blocks may be determined manually. Alternatively, it may be determined automatically with the technique described below. Specifically, a bone image, in which the soft tissue patterns have been erased, is formed with an appropriate value of the parameter and emphasized with image processing, such as edge emphasis processing or conversion into a binary image. Also, a plurality of soft tissue images, in which the bone patterns have been erased, are formed by using various values of the parameter. Thereafter, the level of correlation between the emphasized bone image and each of the soft tissue images is found, and a value of the parameter is found which corresponds to a soft tissue image having the lowest level of correlation. The value of the parameter thus found is determined as the optimum temporary value of the parameter. With such a technique, the optimum temporary value of the parameter for each of the blocks can be determined automatically with a considerably high level of accuracy. In order for the correlation between two images to be found, by way of example, a technique may be employed wherein the square sum of differences between the values of the image signal components, which represent corresponding picture elements in the two images, is calculated, and it is judged that the level of correlation is the lowest when the square sum is the smallest.

In the second method for forming an energy subtraction image in accordance with the present invention, subtraction processing is carried out by using the final value of the parameter, which have been determined for the respective picture elements, and a subtraction image is formed from the subtraction processing. Therefore, the image density (in cases where the image is displayed on a CRT display device, or the like, the luminance), or the contrast, or both the image density and the contrast should preferably be corrected in accordance with the density range, or the contrast range, or both the density range and the contrast range, such that the whole subtraction image may be easy to see.

With the second method for forming an energy subtraction image in accordance with the present invention, the radiation image is divided into a plurality of blocks, and subtraction processing is carried out by using optimum values of the parameter which have been determined for the respective blocks. Therefore, the subtraction processing can be carried out appropriately for every parts of the image. Accordingly, even when the effective radiation absorption coefficient varies for parts of the object having different thicknesses due to non-monochromaticity of the X-rays, the subtraction processing can be carried out appropriately for the whole area of the radiation image, and a subtraction image can be obtained, in which parts to be erased have been erased reliably and which is easy to see.

Also, even when the level of radiation energy fluctuates due to, for example, fluctuations in the X-ray tube voltage for different exposures to the radiation, the subtraction processing can be carried out appropriately such that adverse effects of fluctuations in the level of radiation energy may be eliminated.

The present invention also provides a third method for forming an energy subtraction image during energy subtraction processing wherein, after at least two stimulable phosphor sheets have been exposed to at least two kinds of radiation having different energy distributions and having passed through an object constituted of bones and soft tissues, and a plurality of radiation images of the object, in which different images of at least part of the object are embedded, have been stored on the stimulable phosphor sheets, the stimulable phosphor sheets are exposed to stimulating rays, which cause them to emit light in proportion to the amounts of energy stored thereon during their exposures to the radiation, the amounts of the emitted light are photoelectrically detected and converted into digital image signals, each of which is made up of a series of image signal components, the image signal components of the digital image signals which represent corresponding picture elements in the radiation images are then subtracted from each other with a predetermined parameter, and a difference signal representing an image, in which the patterns of the bones represented by the radiation images have been erased, is thereby obtained, the method for forming an energy subtraction image comprising the steps of:
i) selecting a region of interest in each of said radiation images,
ii) carrying out temporary subtraction processing for the selected region of interest by using various temporary values of the parameter,
iii) rating a plurality of temporary subtraction images, which have been obtained from the temporary subtraction processing,
iv) determining a temporary value of the parameter corresponding to a temporary subtraction image, which has been rated highest, as an optimum value of the parameter, and
v) carrying out final subtraction processing by using the optimum value of the parameter, which has thus been determined.

The present invention further provides a third apparatus for forming an energy subtraction image, which comprises:
i) an image read-out means for exposing stimulable phosphor sheets, on which radiation images have been stored, to stimulating rays, which cause them to emit light in proportion to the amounts of energy stored thereon during their exposures to the radiation, and photoelectricity detecting the emitted light and converting it into digital image signals, each of which is made up of a series of image signal components,
ii) a means for selecting a region of interest in each of said radiation images,
iii) an operation means for carrying out temporary subtraction processing for the selected region of interest by using various temporary values of the parameter,
iv) an optimum parameter value determining means for rating a plurality of temporary subtraction images, which have been obtained from the temporary subtraction processing, and determining a temporary value of the parameter corresponding to a temporary subtraction image, which has been rated highest, as an optimum value of the parameter, and
v) a subtracting operation means for:
after at least two stimulable phosphor sheets have been exposed to at least two kinds of radiation having different energy distributions and having passed through an object constituted of bones and soft tissues, a plurality of radiation images of the object, in which different images of at least part of the object are embedded, have thereby been stored on the stimulable phosphor sheets, and the radiation images have thereafter been read out by said image read-out means from the stimulable phosphor sheets and converted thereby into a plurality of digital image signals, each of which is made up of a series of image signal components,
subtracting the image signal components of the digital image signals from each other by using said optimum value of the parameter, which image signal components represent corresponding picture elements in the radiation images, and thereby generating a difference signal representing an image, in which the patterns of the bones represented by the radiation images have been erased.

In the third method for forming an energy subtraction image in accordance with the present invention, the region of interest may be selected manually. Alternatively, a technique for pattern matching may be employed wherein, for example, a template is used. Specifically, correlation between a predetermined pattern and parts of an image is investigated, and part of the image having a highest level of correlation with respect to the predetermined pattern is selected as the region of interest. As another alternative, various regions of interest may be statistically determined in advance for various types of image.

In the third method for forming an energy subtraction image in accordance with the present invention, final subtraction processing is carried out by using the optimum value of the parameter, which has been determined for the region of interest. Therefore, the image density (in cases where the image is displayed on a CRT display device, or the like, the luminance), or the contrast, or both the image density and the contrast should preferably be corrected in the regions of the image other than the region of interest in accordance with the density range, or the contrast range, or both the density range and the contrast range, such that the whole subtraction image may be easy to see.

With the third method for forming an energy subtraction image in accordance with the present invention, the optimum value of the parameter is determined for the region of interest in the image, and the final subtraction processing is carried out by using the optimum value of the parameter. Therefore, a subtraction image can be obtained in which an image region most important for diagnosis has best possible image quality. Accordingly, even when the effective radiation absorption coefficient varies for parts of the object having different thicknesses due to non-monochromaticity of the X-rays, the subtraction processing can be carried out appropriately for the region of interest in the radiation image, and a subtraction image can be obtained which has good image quality and can serve as an effective tool in, particularly, the efficient and accurate diagnosis of an illness.

Also, even when the level of radiation energy fluctuates due to, for example, fluctuations in the X-ray tube voltage for different exposures to the radiation, the subtraction processing can be carried out appropriately such that adverse effects of fluctuations in the level of radiation energy may be eliminated.

BRIEF DESCRIPTION OF THE DRAWINGS

FIG. 2 is an explanatory view showing an example of a radiation image which is divided into a plurality of blocks in an embodiment of the second method for forming an energy subtraction image in accordance with the present invention.

DESCRIPTION OF THE PREFERRED EMBODIMENTS

The present invention will hereinbelow be described in further detail with reference to the accompanying drawings.

An embodiment of the first method for forming an energy subtraction image in accordance with the present invention will first be described hereinbelow.

Figure 1:
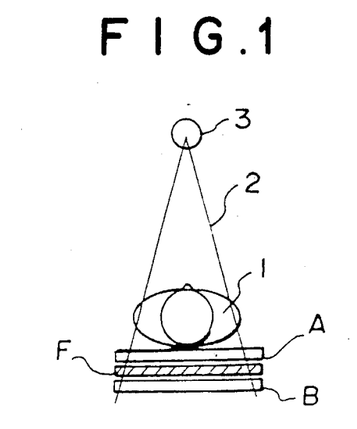
FIG. 1 is an explanatory view showing the step for recording radiation images in an embodiment of the first method for forming an energy subtraction image in accordance with the present invention.

With reference to FIG. 1, stimulable phosphor sheets A and B are placed one upon the other, and a filter F capable of absorbing part of radiation energy is inserted between the stimulable phosphor sheets A and B. The stimulable phosphor sheets A and B are exposed to X-rays 2, which have passed through an object 1 and a phantom 5. (The phantom 5 will be described later.) In this manner, the stimulable phosphor sheets A and B are simultaneously exposed to the X-rays 2 having different energy levels. The image recording operation is thus carried out for one-shot energy subtraction processing. One of one-shot energy subtraction processing methods is disclosed in, for example, U.S. Pat. No. 4,855,598.

In the manner described above, two X-ray images, in which different images of at least part of the object 1 are embedded, are stored on the stimulable phosphor sheets A and B. Thereafter, in an image readout means shown in FIG. 2, the X-ray images are read out from the stimulable phosphor sheets A and B, and digital images signals representing the X-ray images are thereby obtained. Specifically, first, the stimulable phosphor sheet A is moved in the sub-scanning direction indicated by the arrow Y. At the same time, a laser beam 11, which serves as stimulating rays, is produced by a laser beam source 10. The laser beam 11 is deflected by a scanning mirror 12 and caused to scan the stimulable phosphor sheet A in the main scanning directions indicated by the double-headed arrow X. When the stimulable phosphor sheet A is exposed to the laser beam 11, it emits light 13 in proportion to the amount of energy stored thereon during its exposure to the X-rays 2. The emitted light 13 enters a light guide member 14, which is made from a transparent acrylic plate, from its one edge face. The emitted light 13 is guided through repeated total reflection inside of the light guide member 14 and detected by a photomultiplier 15. The photomultiplier 15 generates an image signal S corresponding to the amount of the emitted light 13, i.e. representing the X-ray image stored on the stimulable phosphor sheet A.

Figure 2:
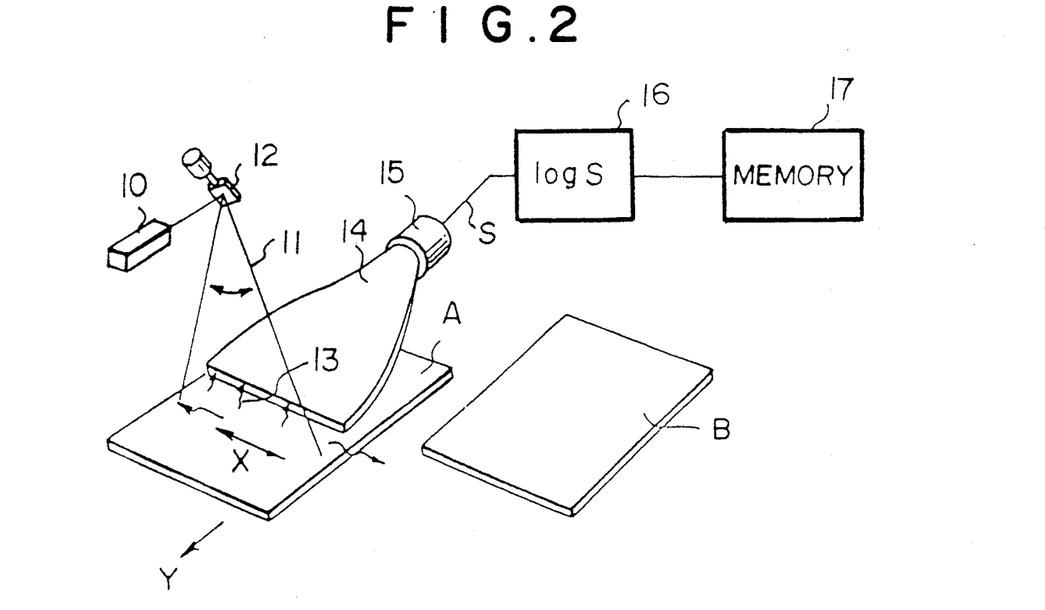
FIG. 2 is a schematic view showing how radiation images are read out from stimulable phosphor sheets.

The image signal S is converted into a digital image signal logSA having logarithmic values (logS) by a logarithmic converter 16 provided with an amplifier and an A/D converter. The digital image signal logSA is stored on a storage medium 17, such as a magnetic disk. Thereafter, the X-ray image stored on the stimulable phosphor sheet B is read out in the same manner as that described above. The digital image signal logSB representing the X-ray image stored on the stimulable phosphor sheet B is stored on the storage medium 17.

Thereafter, subtraction processing is carried out on the digital image signals logSA and logSB, which have been obtained in the manner described above, by using an optimum value of the parameter for a subtraction process. The value of the parameter used during the subtraction processing is determined in the manner described below.

Figure 3A:
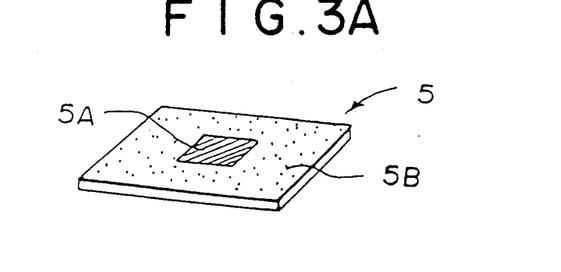
FIGS. 3A and 3B are perspective views showing examples of phantoms employed in embodiments of the first method for forming an energy subtraction image in accordance with the present invention.
Figure 3B:
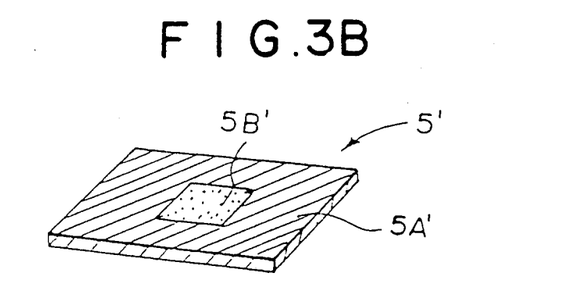

FIG. 3A is a perspective view showing the phantom 5. As illustrated in FIG. 3A, the phantom 5 is constituted of part 5A, which exhibits an equivalent radiation absorption coefficient to bones and which is located in the middle area, and part 5B, which exhibits an equivalent radiation absorption coefficient to soft tissues and which is located in the surrounding areas. FIG. 3B is a perspective view showing a phantom 5'. As illustrated in FIG. 3B, the phantom 5' is constituted of part 5B', which exhibits an equivalent radiation absorption coefficient to soft tissues and which is located in the middle area, and part 5A', which exhibits an equivalent radiation absorption coefficient to bones and which is located in the surrounding areas. When the X-ray images are stored on the stimulable phosphor sheets A and B, the sheets are exposed to the X-rays 2, which have passed through the object 1 and the phantom 5 or 5'. Therefore, images of the phantom 5 or 5' are stored together with the images of the object 1 on the stimulable phosphor sheets A and B. When the X-ray images are then read out from the stimulable phosphor sheets A and B, the image signals thus obtained include the information about the images of the phantom 5 or 5'. (During the image recording operation, the phantoms 5 and 5' may be located side by side or at positions spaced away from each other. In such cases, the image signals obtained from the image read-out operations include the information about the images of the phantoms 5 and 5'.)

The positions of the images of the phantom 5 or 5' in the X-ray images are already known. Therefore, the image signal components representing the images of the phantom 5 or 5' are found from the digital image signals logSA and logSB and used to determine the optimum value of the parameter for subtraction processing.

By way of example, in cases where a subtraction image, in which the bone patterns have been erased, is to be obtained, the digital image signal logSA, which represents the high energy image (i.e. the image stored on the stimulable phosphor sheet A), and the digital image signal logSB, which represents the low energy image (i.e. the image stored on the stimulable phosphor sheet B), are weighted appropriately. The weighting process is carried out such that the image density BH of the image of the part 5A of the phantom in the high energy image and the image density BL of the image of the part 5A in the low energy image become equal to each other. Thereafter, the weighted image signals corresponding to the high energy image and the low energy image are subtracted from each other.

Specifically, the subtraction process is expressed as $$Ssub = BL \cdot logSA - BH \cdot log SB$$

In this manner, an image signal Ssub representing a subtraction image is obtained. In the subtraction image, the bone patterns have been erased. Therefore, a soft tissue image can thus be obtained.

In the manner described above, the value of the parameter, BH/BL, is determined from the difference (ratio) between the image density BH of the image of the part 5A of the phantom 5 in the high energy image and the image density BL of the image of the part 5A in the low energy image.

In cases where a subtraction image, in which the soft tissue patterns have been erased, is to be obtained, a value of the parameter is determined such that the image of the part 5B' of the phantom 5' becomes erased in a subtraction image. Thereafter, subtraction processing is carried out by using the value of the parameter thus determined.

Techniques for carrying out subtraction processing are disclosed in, for example, U.S. Pat. Nos. 4,590,517 and 4,855,598, and Japanese Unexamined Patent Publication No. 58(1983)-163339.

An embodiment of the second method for forming an energy subtraction image in accordance with the present invention will be described hereinbelow.

Figure 4A:
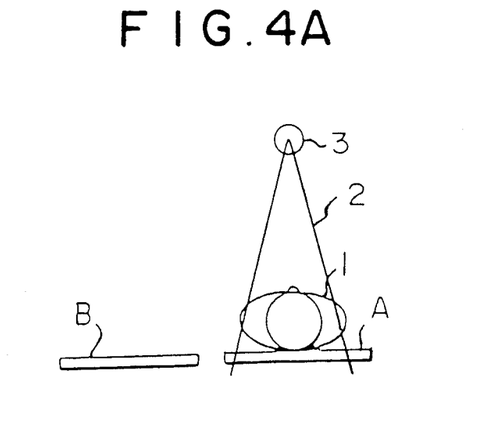
FIGS. 4A and 4B are explanatory views showing examples of the steps for recording radiation images in embodiments of the second method for forming an energy subtraction image in accordance with the present invention.

With reference to FIG. 4A, stimulable phosphor sheets A and B are sequentially exposed to X-rays 2, which have passed through an object 1 constituted of bones and soft tissues, such as the lung fields and blood vessels, and which have different energy levels. Specifically, first, an X-ray image of the object 1 is stored on the stimulable phosphor sheet A. Thereafter, the stimulable phosphor sheet A is quickly removed from the position for exposure to the X-rays 2, and the stimulable phosphor sheet B is quickly set at the position for exposure to the X-rays 2. At the same time, the tube voltage of the X-ray source 3 is changed so that it produces the X-rays 2 having a different energy level. In this manner, an X-ray image of the object 1 is stored on the stimulable phosphor sheet B with the X-rays 2 having the different energy level. The positions of the stimulable phosphor sheets A and B with respect to the position of the object 1 are kept the same.

Figure 4B:
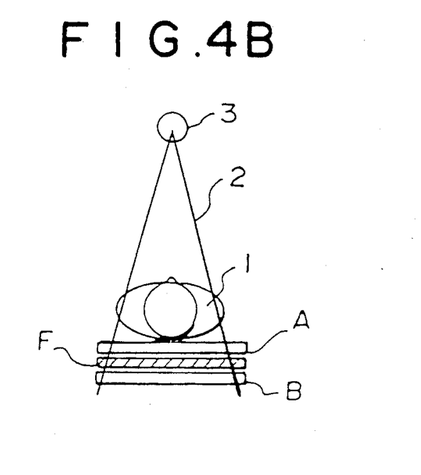

Alternatively, an image recording operation may be carried out in the manner shown in FIG. 4B. With reference to FIG. 4B, stimulable phosphor sheets A and B are placed one upon the other, and a filter F capable of absorbing part of radiation energy is inserted between the stimulable phosphor sheets A and B. The stimulable phosphor sheets A and B are exposed to X-rays 2, which have passed through an object 1. In this manner, the stimulable phosphor sheets A and B are simultaneously exposed to the X-rays 2 having different energy levels. The image recording operation is thus carried out for one-shot energy subtraction processing.

In the manner described above, two X-ray images, in which different images of at least part of the object 1 are embedded, are stored on the stimulable phosphor sheets A and B. Thereafter, in the image readout means shown in FIG. 2, the X-ray images are read out from the stimulable phosphor sheets A and B in the same manner as that described above, and digital image signals logSA and logSB representing the X-ray images are thereby obtained.

Thereafter, subtraction processing is carried out on the digital image signals logSA and logSB, which have been obtained in the manner described above, by using an optimum value of the parameter for a subtraction process. The value of the parameter used during the subtraction processing is determined in the manner described below. Thereafter, subtraction processing is carried out by using the value of the parameter thus determined. From the subtraction processing, a soft tissue image, in which the bone patterns have been erased, or a bone image, in which the soft tissue patterns have been erased, can be obtained.

How the value of the parameter is determined will be described hereinbelow.

Figure 5:
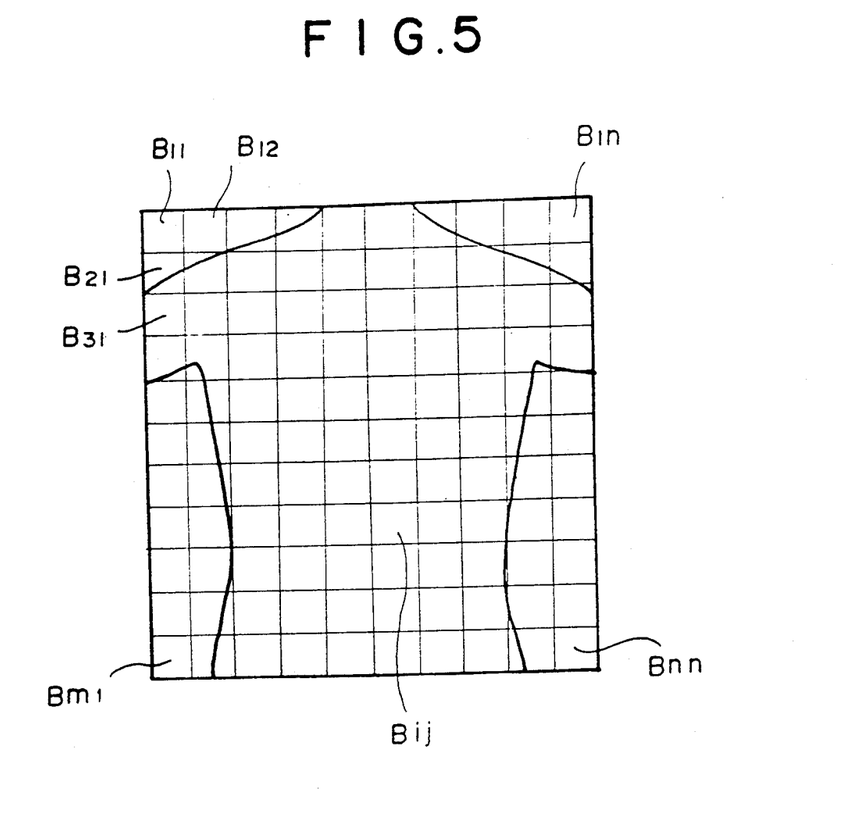

As illustrated in FIG. 5, each of the X-ray images is divided into a plurality of blocks B11, B12, . . . , Bmn. For each of the blocks, subtraction processing is carried out by using a predetermined value of the parameter which is considered as being appropriate. In this manner, a bone image is formed. The bone image is then emphasized with image processing, such as edge emphasis processing or conversion into a binary image. Also, a plurality of soft tissue images, in which the bone patterns have been erased, are formed by using various values of the parameter. Thereafter, the level of correlation between the emphasized bone image and each of the soft tissue images is found, and a value of the parameter is found which corresponds to a soft tissue image having the lowest level of correlation. The value of the parameter thus found is determined as the optimum temporary value of the parameter. In this embodiment, in order for the correlation between two images to be found, the square sum of differences between the values of the image signal components, which represent corresponding picture elements in the two images, is calculated. Specifically, for the emphasized bone image and each of the soft tissue images, which have been formed by using various values of the parameter, calculations are made to find the square sum, $\Sigma(SBij - STij)^2$, of differences between the values SBij of the image signal components, which represent the picture elements in the emphasized bone image, and the values STij of the image signal components, which represent corresponding picture elements in a soft tissue image. Thereafter, a soft tissue image associated with the smallest square sum is found, and the value of the parameter which was employed during the formation of said soft tissue image is determined as the optimum temporary value of the parameter. This is because, the smallest square sum indicates that the bone patterns have been erased to the highest extent.

In the manner described above, the optimum temporary value of the parameter is determined for each of the blocks. Thereafter, the optimum temporary value of the parameter thus determined is assigned to the center picture element of each block. As for the picture elements located between the center picture elements of adjacent blocks, a smoothing (interpolation) process is carried out on the temporary values of the parameter, which have been assigned to the center picture elements of the adjacent blocks. The smoothing (interpolation) process is carried out such that the value of the parameter changes continuously between adjacent picture elements. In this manner, final values of the parameter are determined for the picture elements of the image.

One of various known interpolation techniques may be used for the smoothing (interpolation) process.

Thereafter, subtraction processing is carried out by using the final values of the parameter which have been determined for the picture elements.

In this embodiment, the bone image is formed by using a predetermined value of the parameter and emphasized. The levels of correlation between the emphasized bone image and a plurality of the soft tissue images formed with various values of the parameter are investigated. From the levels of correlation thus found, the optimum temporary values of the parameter are determined. Alternatively, a soft tissue image may be formed by using a predetermined value of the parameter and emphasized. The levels of correlation between the emphasized soft tissue image and a plurality of bone images formed with various values of the parameter may then be investigated. From the levels of correlation thus found, the optimum temporary values of the parameter may be determined.

An embodiment of the third method for forming an energy subtraction image in accordance with the present invention will be described hereinbelow.

In this embodiment, two X-ray images, in which different images of at least part of the object 1 are embedded, are stored on the stimulable phosphor sheets A and B in the same manner as that described above with reference to FIG. 4A or 4B. Thereafter, in the image read-out means shown in FIG. 2, the X-ray images are read out from the stimulable phosphor sheets A and B in the same manner as that described above, and digital image signals logSA and logSB representing the X-ray images are thereby obtained.

Thereafter, subtraction processing is carried out on the digital image signals log SA and logSB, which have been obtained in the manner described above, by using an appropriate value of the parameter for a subtraction process. The value of the parameter used during the subtraction processing is determined in the manner described below. Thereafter, subtraction processing is carried out by using the value of the parameter thus determined. From the subtraction processing, a soft tissue image, in which the bone patterns have been erased, or a bone image, in which the soft tissue patterns have been erased, can be obtained.

How the value of the parameter is determined will be described hereinbelow.

Figure 6:
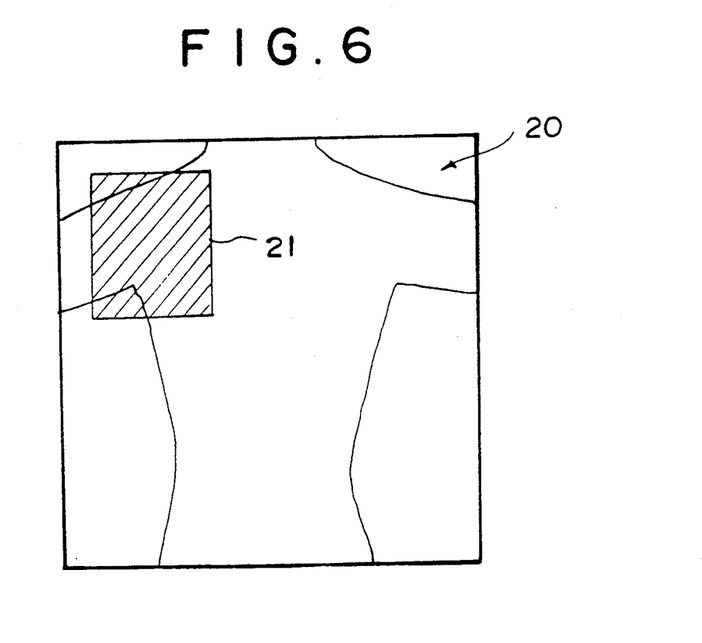
FIG. 6 is an explanatory view showing an example of a radiation image in which a region of interest is selected in an embodiment of the third method for forming an energy subtraction image in accordance with the present invention.

As illustrated in FIG. 6, a region of interest 21 (e.g. a region corresponding to a shoulder joint) is selected in an X-ray image 20.

The region of interest 21 may be selected manually. Alternatively, it may be selected with a pattern matching technique. By way of example, a plurality of templates are prepared, and a template for the shoulder joint is selected therefrom. Correlation between the template thus selected and parts of an image in the vicinity of the pattern of the shoulder joint is investigated. Part of the image having a highest level of correlation with respect to the template is selected as the region of interest. As another alternative, positions and sizes of regions of interest are determined in advance for various types of regions of interest, and a region of interest may be selected therefrom automatically. For example, in the cases of the shoulder joint, the left (or right) region at the upper part of an image is selected. As the template, a temporary bone image, which has been obtained in advance from energy subtraction processing, may be employed. In such cases, the accuracy, with which the value of the parameter is determined, can be kept very high.

Thereafter, temporary subtraction processing operations are carried out for the selected region of interest by using various predetermined temporary values of the parameter. Specifically, temporary values of the parameter are set which vary slightly from one another within a predetermined range (e.g. within a range of several percent), and subtracting operations are carried out by using them. In this manner, a plurality of temporary energy subtraction images are obtained, in which the bone patterns (or the soft tissue patterns) have been erased.

Thereafter, the corresponding regions of interest in the plurality of the temporary subtraction images (soft tissue images) are rated. For this purpose, high-frequency components of the image signal components corresponding to the region of interest in each of the temporary subtraction images are eliminated by carrying out unsharp mask processing on the image signal components. Thereafter, the root-mean-square value (RMS value) is calculated from the image signal components, which have been obtained from the unsharp mask processing. A temporary subtraction image associated with the smallest RMS value is rated highest. The temporary value of the parameter corresponding to the temporary subtraction image, which has thus been rated highest, is determined as an optimum value of the parameter. The smallest RMS value indicates that the bone patterns have been erased to the highest extent.

Thereafter, final subtraction processing is carried out by using the optimum value of the parameter, which has thus been determined, for the region of interest.

Figure 7:
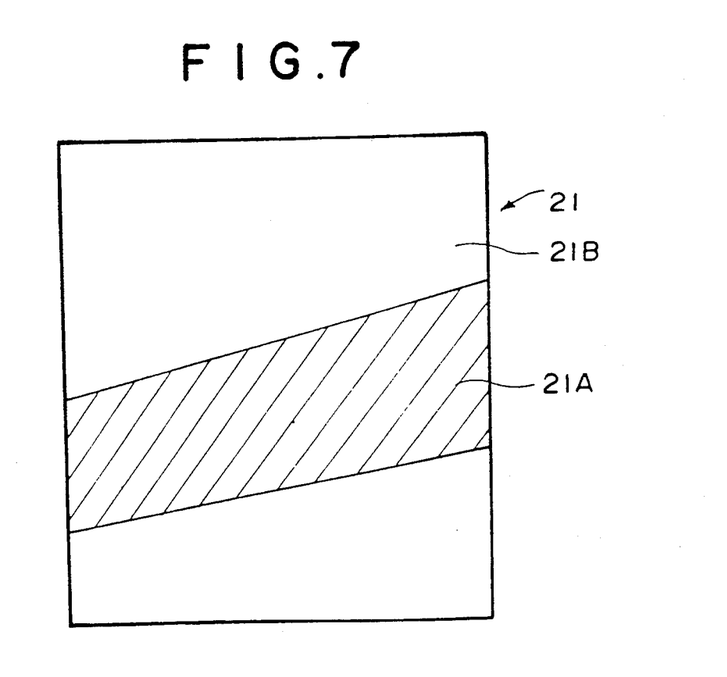
FIG. 7 is an explanatory view showing an example of a region of interest in a radiation image, which region is selected in another embodiment of the third method for forming an energy subtraction image in accordance with the present invention.

FIG. 7 is an explanatory view showing an example of a region of interest in a radiation image, which region is selected in another embodiment of the third method for forming an energy subtraction image in accordance with the present invention. In this example, bone patterns are present in a region of interest 21. In this embodiment, the region of interest 21 is divided into a bone region 21A and the other region 21B. For this purpose, the image signal components corresponding to the region of interest 21 are converted into binary image signal components, and small areas represented by the binary image signal components are eliminated. Alternatively, unsharp mask processing is carried out on the image signal components corresponding to the region of interest 21, and image signal components obtained from the unsharp mask processing are then converted into binary image signal components.

After the region of interest 21 has been divided into a bone region 21A and the other region 21B in the manner described above, temporary values of the parameter are set which vary slightly from one another within a predetermined range (e.g. within a range of several percent), and subtracting operations are carried out by using them in the same manner as that in the embodiment described above with reference to FIG. 6. In this manner, a plurality of temporary energy subtraction images are obtained, in which the bone patterns have been erased. From the plurality of the temporary energy subtraction images, a temporary energy subtraction image is found and rated highest in which the difference between the mean image density in the bone region 21A and the mean image density in the other region 21B is smallest, i.e. in which the bone patterns have been erased to the highest extent. The temporary value of the parameter corresponding to the temporary subtraction image, which has thus been rated highest, is determined as an optimum value of the parameter.

As described above, in cases where parts having high contrast (e.g. the bone region and the other region) is present in the region of interest, the image signal components corresponding to the region of interest are converted into binary image signal components. The region of interest is thus divided into two regions, and then temporary subtraction processing is carried out. With this embodiment, the optimum value of the parameter can be determined easily.

In the aforesaid embodiments of the first, second, and third methods for forming an energy subtraction image in accordance with the present invention, two stimulable phosphor sheets A and B are used. The first, second, and third methods for forming an energy subtraction image in accordance with the present invention are also applicable when three or more stimulable phosphor sheets are exposed to several kinds of radiation having different energy levels, digital image signals detected from the stimulable phosphor sheets are then subtracted from one another, and a difference signal is thereby obtained. For example, in cases where three stimulable phosphor sheets are used, a difference signal logSo may be calculated with the formula $$logSo = a \cdot logSA + b \cdot logSB - c \cdot logSC + d$$

wherein a, b, and c denote weighting coefficients, and d denotes a bias component for adjusting such that the image density represented by the difference signal logSo becomes approximately equal to a predetermined level.

Also, in the aforesaid embodiments of the first, second, and third methods for forming an energy subtraction image in accordance with the present invention, the stimulable phosphor sheets A and B are independently exposed to the radiation having different energy levels. Alternatively, the recording of the radiation images on a plurality of stimulable phosphor sheets may be carried out in any of other manners. For example, as disclosed in, for example, U.S. Pat. No. 4,855,598, a stack of stimulable phosphor sheets or a stimulable phosphor sheet-filter stack may be used, and a plurality of radiation images may be recorded with a single simultaneous exposure to radiation. Any of image recording operations may be employed with which a plurality of stimulable phosphor sheets are exposed to several kinds of radiation having different energy levels and having passed through an object.

Additionally, in the aforesaid embodiments of the first and second methods for forming an energy subtraction image in accordance with the present invention, radiation images are stored on the stimulable phosphor sheets and read out therefrom. Alternatively, radiation images may be detected by using an image intensifier. As another alternative, images recorded on sheets of film may be converted into digital image signals by using a film digitizer. No limitation is imposed on how radiation images are detected insofar as digital image signals are obtained.

The energy subtraction processing wherein stimulable phosphor sheets are used is also applicable when, for example, a subtraction image in which a pattern of a medical implement has been erased is to be obtained from radiation images of a human body having the medical implement embedded therein, and when a subtraction image in which a pattern of contrast media has been erased is to be obtained from radiation images of a human body injected with contrast media. Accordingly, the term "bone" as used herein embraces metals, contrast media, and other materials which can be regarded as elements equivalent to bones from the point of view of signal processing. Also, the term "soft tissue" as used herein embraces various substances which exhibit different radiation absorption characteristics from bones and elements equivalent to bones, and the patterns of which can be extracted from radiation images by the energy subtraction processing.

We claim:

1. A method for forming an energy subtraction image during energy subtraction processing wherein a plurality of radiation images of an object constituted of bones and soft tissues, which radiation images have been formed with at least two kinds of radiation having different energy distributions and having passed through the object and in which different images of at least part of the object are embedded, are read out and converted into a plurality of digital image signals, each of which is made up of a series of image signal components, the image signal components of the digital image signals which represent corresponding picture elements in the plurality of the radiation images are then subtracted from each other with a predetermined parameter, and a difference signal representing an image, in which the patterns of the bones or the patterns of the soft tissues represented by the radiation images have been erased, is thereby obtained, the method for forming an energy subtraction image comprising the steps of:
i) during the operation for reading out each of said radiation images, simultaneously reading out each of a plurality of images of a phantom, which at least has part exhibiting an equivalent radiation absorption coefficient to said bones and/or part exhibiting an equivalent radiation absorption coefficient to said soft tissues, together with the image of the object,
ii) finding a value of the parameter, with which the image of the part of said phantom exhibiting an equivalent radiation absorption coefficient to said bones or the image of the part of said phantom exhibiting an equivalent radiation absorption coefficient to said soft tissues, whichever image is to be erased, becomes erased in a subtraction image of said phantom obtained from subtraction processing,
iii) determining the value of the parameter, which has thus been found, as an optimum value of the parameter, and
iv) carrying out subtraction processing by using said optimum value of the parameter.

2. A method as defined in claim 1 wherein said phantom has a thin filter-like shape.

3. A method as defined in claim 1 wherein, in cases where a difference signal representing an image, in which the patterns of the bones represented by said radiation images have been erased, is to be obtained, said phantom is constituted such that the part exhibiting an equivalent radiation absorption coefficient to bones is located in the middle area of said phantom, and the part exhibiting an equivalent radiation absorption coefficient to soft tissues is located in the surrounding areas.

4. A method as defined in claim 1 wherein, in cases where a difference signal representing an image, in which the patterns of the soft tissues represented by said radiation images have been erased, is to be obtained, said phantom is constituted such that the part exhibiting an equivalent radiation absorption coefficient to soft tissues is located in the middle area of said phantom, and the part exhibiting an equivalent radiation absorption coefficient to bones is located in the surrounding areas.

5. A method as defined in claim 1 wherein said phantom is provided with a plurality of parts exhibiting radiation absorption coefficients which change stepwise and which are equivalent to those of various substances, including the bones and soft tissues.

6. A method as defined in claim 1 wherein said radiation images have been stored on stimulable phosphor sheets.

7. A method as defined in claim 6 wherein said radiation images stored on said stimulable phosphor sheets are read out from an image read-out operation in which each said stimulable phosphor sheet is exposed to stimulating rays, which cause it to emit light in proportion to the amount of energy stored thereon during its exposure to radiation, and the emitted light is detected photoelectrically.

8. A method as defined in claim 7 wherein said stimulating rays are a laser beam.

9. An apparatus for forming an energy subtraction image, which comprises:

i) an image read-out means for reading out each of a plurality of radiation images of a phantom, which at least has part exhibiting an equivalent radiation absorption coefficient to said bones and/or part exhibiting an equivalent radiation absorption coefficient to said soft tissues, together with each of a plurality of radiation images of an object, and converting these radiation images into digital image signals,
ii) an optimum parameter value determining means for finding a value of a parameter for a subtraction process, with which value the image of the part of said phantom exhibiting an equivalent radiation absorption coefficient to said bones or the image of the part of said phantom exhibiting an equivalent radiation absorption coefficient to said soft tissues, whichever image is to be erased, becomes erased in a subtraction image, which is obtained from subtraction processing carried out on regions in which said radiation images of said phantom were recorded, and determining the value of the parameter, which has thus been found, as an optimum value of the parameter, and
iii) a subtracting operation means for:
after the plurality of said radiation images of said object constituted of bones and soft tissues, which radiation images have been formed with at least two kinds of radiation having different energy distributions and having passed through said object and in which different images of at least part of said object are embedded, are read out by said image read-out means and converted thereby into a plurality of digital image signals, each of which is made up of a series of image signal components,
subtracting the image signal components of the digital image signals from each other by using said optimum value of the parameter, which image signal components represent corresponding picture elements in the plurality of said radiation images, and thereby generating a difference signal representing an image, in which the patterns of the bones or the patterns of the soft tissues represented by said radiation images have been erased.

10. An apparatus as defined in claim 9 wherein said phantom has a thin filter-like shape.

11. An apparatus as defined in claim 9 wherein, in cases where a difference signal representing an image, in which the patterns of the bones represented by said radiation images have been erased, is to be obtained, said phantom is constituted such that the part exhibiting an equivalent radiation absorption coefficient to bones is located in the middle area of said phantom, and the part exhibiting an equivalent radiation absorption coefficient to soft tissues is located in the surrounding areas.

12. An apparatus as defined in claim 9 wherein, in cases where a difference signal representing an image, in which the patterns of the soft tissues represented by said radiation images have been erased, is to be obtained, said phantom is constituted such that the part exhibiting an equivalent radiation absorption coefficient to soft tissues is located in the middle area of said phantom, and the part exhibiting an equivalent radiation absorption coefficient to bones is located in the surrounding areas.

13. An apparatus as defined in claim 9 wherein said phantom is provided with a plurality of parts exhibiting radiation absorption coefficients which change stepwise and which are equivalent to those of various substances, including the bones and soft tissues.

14. An apparatus as defined in claim 9 wherein said radiation images have been stored on stimulable phosphor sheets.

15. An apparatus as defined in claim 14 wherein said image read-out means reads out each of said radiation images stored on said stimulable phosphor sheets from an image read-out operation in which each said stimulable phosphor sheet is exposed to stimulating rays, which cause it to emit light in proportion to the amount of energy stored thereon during its exposure to radiation, and the emitted light is detected photoelectrically.

16. An apparatus as defined in claim 15 wherein said stimulating rays are a laser beam.

17. A method for forming an energy subtraction image during energy subtraction processing wherein a plurality of radiation images of an object constituted of bones and soft tissues, which radiation images have been formed with at least two kinds of radiation having different energy distributions and having passed through the object and in which different images of at least part of the object are embedded, are read out and converted into a plurality of digital image signals, each of which is made up of a series of image signal components, the image signal components of the digital image signals which represent corresponding picture elements in the plurality of the radiation images are then subtracted from each other with a predetermined parameter, and a difference signal representing an image, in which the patterns of the bones or the patterns of the soft tissues represented by the radiation images have been erased, is thereby obtained, the method for forming an energy subtraction image comprising the steps of:
  i) dividing each of said radiation images into a plurality of blocks,
  ii) determining an optimum temporary value of the parameter for each of said blocks,
  iii) determining a final value of the parameter for each of picture elements of the radiation image by carrying out a smoothing process on the temporary values of the parameter, which have been determined for the plurality of said blocks, such that the value of the parameter changes continuously between adjacent picture elements, and
  iv) carrying out subtraction processing by using the final values of the parameter which have been determined for the picture elements.

18. A method as defined in claim 17 wherein said optimum temporary value of the parameter for each of said blocks is determined from an operation comprising the steps of:
  a) forming a bone image, in which the soft tissue patterns have been erased, by using an appropriate value of the parameter,
  b) emphasizing said bone image,
  c) forming a plurality of soft tissue images, in which the bone patterns have been erased, by using various values of the parameter,
  d) finding the level of correlation between said emphasized bone image and each of said soft tissue images,
  e) finding a value of the parameter which corresponds to a soft tissue image having the lowest level of correlation, and
  f) determining the value of the parameter, which has thus been found, as said optimum temporary value of the parameter.

19. A method as defined in claim 17 wherein said radiation images have been stored on stimulable phosphor sheets.

20. A method as defined in claim 19 wherein said radiation images stored on said stimulable phosphor sheets are read out from an image read-out operation in which each said stimulable phosphor sheet is exposed to stimulating rays, which cause it to emit light in proportion to the amount of energy stored thereon during its exposure to radiation, and the emitted light is detected photoelectrically.

21. A method as defined in claim 20 wherein said stimulating rays are a laser beam.

22. An apparatus for forming an energy subtraction image, which comprises:
  i) an image read-out means for reading out radiation images and converting them into digital image signals,
  ii) a temporary parameter value determining means for determining an optimum temporary value of a parameter for a subtraction process, said temporary value of the parameter being determined for each of blocks, into which each of said radiation images has been divided,
  iii) a final parameter value determining means for determining a final value of the parameter for each of picture elements of the radiation image by carrying out a smoothing process on the temporary values of the parameter, which have been determined for the plurality of said blocks, such that the value of the parameter changes continuously between adjacent picture elements, and
  iv) a subtracting operation means for:
    after a plurality of radiation images of an object constituted of bones and soft tissues, which radiation images have been formed with at least two kinds of radiation having different energy distributions and having passed through said object and in which different images of at least part of said object are embedded, are read out by said image read-out means and converted thereby into a plurality of digital image signals, each of which is made up of a series of image signal components,
    subtracting the image signal components of the digital image signals from each other by using said final values of the parameter, which image signal components represent corresponding picture elements in the plurality of said radiation images, and thereby generating a difference signal representing an image, in which the patterns of the bones or the patterns of the soft tissues represented by said radiation images have been erased.

23. An apparatus as defined in claim 22 wherein said temporary parameter value determining means determines said optimum temporary value of the parameter for each of said blocks from an operation comprising the steps of:
  a) forming a bone image, in which the soft tissue patterns have been erased, by using an appropriate value of the parameter,
  b) emphasizing said bone image, c) forming a plurality of soft tissue images, in which the bone patterns have been erased, by using various values of the parameter, d) finding the level of correlation between said emphasized bone image and each of said soft tissue images, e) finding a value of the parameter which corresponds to a soft tissue image having the lowest level of correlation, and f) determining the value of the parameter, which has thus been found, as said optimum temporary value of the parameter.

24. An apparatus as defined in claim 22 wherein said radiation images have been stored on stimulable phosphor sheets.

25. An apparatus as defined in claim 24 wherein said image read-out means reads out each of said radiation images stored on said stimulable phosphor sheets from an image read-out operation in which each said stimulable phosphor sheet is exposed to stimulating rays, which cause it to emit light in proportion to the amount of energy stored thereon during its exposure to radiation, and the emitted light is detected photoelectrically.

26. A method as defined in claim 25 wherein said stimulating rays are a laser beam.

27. A method for forming an energy subtraction image during energy subtraction processing wherein, after at least two stimulable phosphor sheets have been exposed to at least two kinds of radiation having different energy distributions and having passed through an object constituted of bones and soft tissues, and a plurality of radiation images of the object, in which different images of at least part of the object are embedded, have been stored on the stimulable phosphor sheets, the stimulable phosphor sheets are exposed to stimulating rays, which cause them to emit light in proportion to the amounts of energy stored thereon during their exposures to the radiation, the amounts of the emitted light are photoelectrically detected and converted into digital image signals, each of which is made up of a series of image signal components, the image signal components of the digital image signals which represent corresponding picture elements in the radiation images are then subtracted from each other with a predetermined parameter, and a difference signal representing an image, in which the patterns of the bones represented by the radiation images have been erased, is thereby obtained, the method for forming an energy subtraction image comprising the steps of:

i) selecting a region of interest in each of said radiation images, ii) carrying out temporary subtraction processing for the selected region of interest by using various temporary values of the parameter, iii) rating a plurality of temporary subtraction images, which have been obtained from the temporary subtraction processing, iv) determining a temporary value of the parameter corresponding to a temporary subtraction image, which has been rated highest, as an optimum value of the parameter, and v) carrying out final subtraction processing by using the optimum value of the parameter, which has thus been determined.

28. A method as defined in claim 27 wherein said region of interest is selected by using a pattern matching technique.

29. A method as defined in claim 27 wherein said temporary subtraction images are rated from an operation comprising the steps of:

a) eliminating high-frequency components from the image signal components corresponding to the region of interest in each of said temporary subtraction images by carrying out unsharp mask processing on the image signal components, b) calculating a root-mean-square value from the image signal components, which have been obtained from the unsharp mask processing, and c) placing the highest rating value on a temporary subtraction image associated with the smallest root-mean-square value.

30. A method as defined in claim 27 wherein, in cases where parts having high contrast is present in said region of interest, the image signal components corresponding to said region of interest are converted into binary image signal components, said region of interest is thereby divided into two regions, and thereafter temporary subtraction processing is carried out.

31. An apparatus for forming an energy subtraction image, which comprises:

i) an image read-out means for exposing stimulable phosphor sheets, on which radiation images have been stored, to stimulating rays, which cause them to emit light in proportion to the amounts of energy stored thereon during their exposures to the radiation, and photoelectrically detecting the emitted light and converting it into digital image signals, each of which is made up of a series of image signal components, ii) a means for selecting a region of interest in each of said radiation images, iii) an operation means for carrying out temporary subtraction processing for the selected region of interest by using various temporary values of the parameter, iv) an optimum parameter value determining means for rating a plurality of temporary subtraction images, which have been obtained from the temporary subtraction processing, and determining a temporary value of the parameter corresponding to a temporary subtraction image, which has been rated highest, as an optimum value of the parameter, and v) a subtracting operation means for:

after at least two stimulable phosphor sheets have been exposed to at least two kinds of radiation having different energy distributions and having passed through an object constituted of bones and soft tissues, a plurality of radiation images of the object, in which different images of at least part of the object are embedded, have thereby been stored on the stimulable phosphor sheets, and the radiation images have thereafter been read out by said image read-out means from the stimulable phosphor sheets and converted thereby into a plurality of digital image signals, each of which is made up of a series of image signal components, subtracting the image signal components of the digital image signals from each other by using said optimum value of the parameter, which image signal components represent corresponding picture elements in the radiation images, and thereby generating a difference signal representing an image, in which the patterns of the bones represented by the radiation images have been erased.

32. An apparatus as defined in claim 31 wherein said means for selecting a region of interest select said region of interest by using a pattern matching technique.

33. An apparatus as defined in claim 31 wherein said optimum parameter value determining means rates said temporary subtraction images from an operation comprising the steps of:
  a) eliminating high-frequency components from the image signal components corresponding to the region of interest in each of said temporary subtraction images by carrying out unsharp mask processing on the image signal components,
  b) calculating a root-mean-square value from the image signal components, which have been obtained from the unsharp mask processing, and
  c) placing the highest rating value on a temporary subtraction image associated with the smallest root-mean-square value.

34. An apparatus as defined in claim 31 wherein, in cases where parts having high contrast is present in said region of interest, said operation means converts the image signal components corresponding to said region of interest into binary image signal components, thereby divides said region of interest into two regions, and thereafter carries out temporary subtraction processing.

* * * * *